(12) United States Patent
Duval

(10) Patent No.: US 7,173,536 B2
(45) Date of Patent: Feb. 6, 2007

(54) SUBSTANCE DETECTION AND ALARM USING A SPECTROMETER BUILT INTO A STEERING WHEEL ASSEMBLY

(76) Inventor: Landon Duval, 1200 Pacific Coast Hwy., #410, Huntington Beach, CA (US) 92648

( * ) Notice: Subject to any disclaimer, the term of this patent is extended or adjusted under 35 U.S.C. 154(b) by 214 days.

(21) Appl. No.: 10/928,328

(22) Filed: Aug. 28, 2004

(65) Prior Publication Data

US 2006/0044144 A1    Mar. 2, 2006

(51) Int. Cl.
  *G08B 23/00*    (2006.01)
(52) U.S. Cl. ............... 340/576; 340/438; 250/339.12; 356/326
(58) Field of Classification Search ............... 340/576
  See application file for complete search history.

(56) References Cited

U.S. PATENT DOCUMENTS

| | | | |
|---|---|---|---|
| 3,818,434 A * | 6/1974 | Gotoh et al. ............... 340/576 |
| 4,090,078 A | 5/1978 | Heim |
| 4,277,251 A | 7/1981 | Leichnitz |
| 4,363,635 A | 12/1982 | Hutson |
| 4,594,509 A | 6/1986 | Simon et al. |
| 4,649,027 A | 3/1987 | Talbot |
| 4,749,553 A | 6/1988 | Lopez et al. |
| 4,849,180 A | 7/1989 | Fukui |
| 4,905,498 A | 3/1990 | O'Donnell et al. |
| 5,220,919 A | 6/1993 | Phillips et al. |
| 5,376,555 A | 12/1994 | Forrester et al. |
| 5,729,619 A * | 3/1998 | Puma .......................... 382/115 |
| 5,743,349 A | 4/1998 | Steinberg |
| 5,793,292 A * | 8/1998 | Ivey, Jr. ....................... 340/576 |
| 5,907,407 A * | 5/1999 | Atkinson et al. ............ 356/437 |
| 5,969,615 A * | 10/1999 | Ivey et al. ................... 340/576 |
| 6,031,233 A | 2/2000 | Levin et al. |
| 6,075,444 A | 6/2000 | Soh'ege et al. |
| 6,097,480 A | 8/2000 | Kaplan |
| 6,183,418 B1 | 2/2001 | Kuennecke |
| 6,620,108 B2 * | 9/2003 | Duval et al. .............. 340/573.1 |
| 6,819,248 B2 * | 11/2004 | Gotfried ................... 340/573.1 |
| 6,853,956 B2 * | 2/2005 | Ballard et al. .............. 702/183 |
| 2003/0087452 A1 | 5/2003 | Ratogi et al. |

* cited by examiner

*Primary Examiner*—Daniel Wu
*Assistant Examiner*—Eric M. Blount
(74) *Attorney, Agent, or Firm*—Gene Scott, Patent Law & Venture Group

(57) ABSTRACT

A spectrometer for infrared reflectance measurements of samples for identification of the sample materials is built into a steering wheel assembly. The spectrometer includes a window and optics on a bench adjacent the window, so that the optics will be aligned with the sample when the device is placed in optical alignment with or directly against the sample. The optics include a broad-band IR light source (ordinary lamp) shining onto an acousto-optic tunable filter (AOTF), which passes narrow-band IR light with a swept frequency; a lens focusing the IR through the window onto the sample; and a reflectance detector aligned with the window of the spectrometer to pick up reflected light. A computer, which may be mounted in the spectrometer, compares the detected reflectance spectrum with stored sample data spectra, and identifies the material or the components of the material and their proportions. When a control substance is detected an alarm signal is produced.

5 Claims, 3 Drawing Sheets

SUBSTANCE DETECTION AND ALARM USING A SPECTROMETER BUILT INTO A STEERING WHEEL ASSEMBLY

BACKGROUND OF THE INVENTION

1. Related Applications

This application is related to co-pending applications which describe related apparatii and methods for detecting vapors in an automotive steering wheel structure; including an application entitled, "Steering Wheel Vapor Collection and Sensing System Using Suction," which was filed on Jul. 26, 2004 as Ser. No. 10/899,826; and an application entitled "Steering Wheel Vapor Collection and Sensing System Using a Chemical Element," which was filed on Aug. 12, 2004 as Ser. No. 10/917,694.

2. Incorporation by Reference

Applicant hereby incorporates herein by reference, the U.S. patents and U.S. patent applications, described in the Description of Related Art section of this application; specifically by document number: 20030087452; U.S. Pat. Nos. 4,090,078; 4,277,251; 4,363,635; 4,649,027; 4,749,553; 4,849,180; 4,905,498; 5,055,268; 5,220,919; 5,376,555; 5,743,349; 6,075,444; 6,097,480; 6,183,418; 6,620,108, 6,031,233 and 4,594,509.

3. Field of the Invention

This invention relates generally to light spectroscopy and especially to the detection of trace amounts of an alcohol containing substance carried by perspiration such as a person's skin surfaces. This invention is related to analyzers used by law enforcement agencies where the breath of a driver is subject to analysis; and more particularly to a steering wheel mounted structure for collection and detection of such vapors through the use of infrared spectrometry.

4. Background Details and Description of Related Art

Plastics and many other materials can be identified by their infrared (IR) reflectance or transmission spectrum. Each type—nylon, polyethylene, etc.—has its own IR characteristic spectrum. If a generally constant-intensity IR beam incident on a plastic is scanned through a range of wavelengths, and the intensity of the reflected or transmitted light is measured as a function of the wavelength, then the measured spectrum can be used to identify the type of plastic.

In addition, mixtures of plastics or other materials can be quantitatively analyzed. The reflectance or transmission spectrum of a sample can show that it is, for example, 50% nylon and 50% polyethylene. The proportion of octane in a sample of gasoline can be measured, or the amount of fat in a chocolate bar. Likewise, trace amounts of ethanol can be detected as present on the hands or as liberated in the sweat on ones hands.

Several types of IR spectrometers are known. Some use a diffraction grating or FTIR technology; these are bulky, delicate, and slow. They are not suited to rapid identification of substances or for rugged use.

Another type uses an acousto-optical tunable filter (AOTF) such as that disclosed in U.S. Pat. No. 5,120,961 to Levin et al, U.S. Pat. No. 4,883,963 to Kemeny et al, and U.S. Pat. No. 4,052,121 to Chang, the entire contents of which patents are fully incorporated herein by reference. The acousto-optic tunable filter (AOTF) is based on a birefringent crystal, such as a crystal of $TeO_2$ (tellurium dioxide) which acts as an electronically tunable narrowband filter, in which diffraction results from an acoustic pressure wave in the crystal.

If an acoustic wave traverses the crystal, the compression or pressure inside the crystal varies as the wave passes, causing a periodic variation in the refractive index. As crystal compression varies, so does the birefringence of a beam of unpolarized visible or IR light that passes through the crystal in a direction normal to its entry and exit faces. When sound having a certain acoustic wavelength is present in the crystal, the crystal acts as an optical filter passing that infrared light having a wavelength proportional to the acoustic wavelength. Because the birefringent crystal acts as a frequency-selective narrowband optical filter, and sound of any acoustic wavelength can be passed through the crystal, any desired visible or IR wavelength can be selected at will, just by varying the frequency of an acoustic driver.

The acoustic driver is a second crystal of the piezo-electric type (quartz or lithium niobate, LiNbo), which is an acoustic transducer. Such a piezo crystal changes its size when subjected to an RF field.

Birefringent $TeO_2$ bonded to piezo-electric LiNo, in which the LiNo is subjected to a sinusoidally-varying AC voltage applied across the face parallel to the birefringent crystal, will act as a swept-frequency optical filter. When the AC voltage impressed across the piezo crystal is at high radio-frequencies (RF) of 20–100 MHz, the acoustic wavelength corresponds to infrared (IR) light wavelengths. (One MHz is one million cycles per second.) The impressed voltage may be obtained from digital synthesizer, controlled by a software algorithm which determines the frequencies generated, and which can sequentially scan or hop in a random access fashion.

Broad-spectrum white light (from a halogen lamp, for example) which shines through the crystal (parallel to the junction between the birefringent and piezo-crystals) will emerge as a beam having one optical frequency corresponding to the acoustic frequency of sound in the piezo crystal. Typical IR wavelengths selected by the AOTF filter are from 1–3 microns (near infrared) or from 2–5 microns (mid-infrared).

The tuned infrared beam can then be either reflected from, or transmitted through, a sample to determine the spectrum and identification of the sample. To identify the sample of plastic or other material, the swept-frequency beam of light is made to shine onto a surface of the undetermined material, which will reflect different proportions of the light falling onto it at each of the various frequencies. A photodetector can be used to pick up the reflected light and turn it into an electrical signal. Electronic circuits can then plot the pattern of the material's reflectance of IR or light frequency, and use that pattern to identify the material by matching the pattern with known patterns corresponding to various materials.

IR spectrometers can measure the proportion of a compound in a sample, by calibrating the circuitry to recognize samples having various percentages of compounds. The percentage can also be calculated according to Beer's law.

Compared to other spectrometer instruments such as diffraction gratings and the FTIR, the AOTF spectrometer has the advantages of no moving parts, high speed wavelength tuning, and small size. However, previous AOTF spectrometers have consisted of a fairly bulky and heavy electronics and optical modules, so that its use is limited to the laboratory. The present spectrometer overcomes these problems and provides compact, light weight solutions ideal for the applications described herein and use within a steering wheel housing.

The following references describe the means by which substances such as ethanol are detected and measured presently.

Levin, et al, U.S. Pat. No. 6,031,233 discloses a handheld device for infrared reflectance measurements of samples for identification of the sample materials in a self-contained portable unit built into a handheld housing. The housing includes a window and optics on a bench adjacent the window, so that the optics will be aligned with the sample when the device is placed directly against the sample. The optics include a broad-band IR light source t (ordinary lamp) shining onto an acousto-optic tunable filter (AOTF), which passes narrow-band IR light with a swept frequency; a lens focusing the IR through the window onto the sample; and a reflectance detector aligned with the window of the housing to pick up reflected light. A computer, which may be mounted in the housing, compares the detected reflectance spectrum with stored sample data spectra, and identifies the material or the components of the material and their proportions. Inclusion of all the parts inside the housing allows the device to be portable; this is made possible by the alignment of the lamp, AOTF filter, lens, window, and detector, which has high optical efficiency, and by elimination of optical fibers.

Simon, et al, U.S. Pat. No. 4,594,509 discloses an infrared spectrometer comprising a first optical means for focusing a beam of light in a point-shaped area of a sample (19), second optical means for focusing upon a detector (26) the light emitted by the sample, and third optical means permitting the visual observation of the point-shaped area (19). The second optical means of this arrangement are so designed that they pick up the light reflected by the point-shaped area (19). The arrangement of the invention permits measurements to be performed on extremely small areas and even on samples which are not or hardly pervious to light in the infrared range.

Ratogi, et al. 20030087452, discloses a method of making a bismuth molybdate precursor solution using a metallorganic decomposition (MOD) process consisting of the formation of a precursor sol of hexanoates of Bismuth (Bi) and Molybdenum (Mo). The precursor solution is used to make thin film of Bismuth molybdate by spin coating and spray pyrolysis. The bismuth molybdate films have the useful alpha and gamma phases having high sensitivity to ethanol gas, the detection of the ethanol gas is based upon the change of electrical conductivity of a thick film of the semiconductor oxide sensing element resulting from the ethanol gas in an oxygen-containing atmosphere. When the drying is effected by spray pyrolysis, quite thick films with high adhesion have been produced over different substrates, including quartz. The thin film of the present invention made by spray pyrolysis has a very fast response to ethanol detection eg typically 5 seconds.

Heim, U.S. Pat. No. 4,090,078 describes a method for determining the alcohol content in the exhaling respiratory air using an alcohol measuring instrument and measuring the alcohol content when the exhaling air transmits the determined value of the alcohol concentration. This determined value of alcohol concentration occurs when the time variation related to the height of the alcohol signal is below a predetermined threshold value and the velocity of flow of the exhaling air is above a given value and is maintained without interruption for a given time. The apparatus includes an infrared measuring instrument which is connected into the respiratory air current and measures the alcohol concentration of the exhaling air. This value is applied to an indicator through a linear gate when an AND-gate is triggered by threshold comparators and a timing element activated by a threshold comparator.

Leichnitz, U.S. Pat. No. 4,277,251 describes a method of determining the alcohol content of air exhaled by a person using a flow through testing tube having an alcohol indicating material therein and a sampling tube to which the air is directed which has a material therein for retaining the alcohol of the breathing air and also using a suction pump comprises cooling the sampling tube, passing the exhaled air through the cooled sampling tube, measuring a volume of the air passing through the cooled sampling tube, heating the sampling tube and connecting the suction pump to the sampling tube to suck flushing air through the heated tube and then through the testing tube. The sampling tube advantageously contains a silica gel to retain the alcohol therein. The volume measuring device may be a measuring bag.

Hutson, U.S. Pat. No. 4,363,635 describes a method and apparatus for discriminating between alcohol and acetone in a breath sample and accurately measuring the alcohol level when acetone is present in the sample. The breath sample is measured with two different types of detectors and their outputs compared. One detector uses the principles of infrared (IR) absorption, the other detector is a semiconductor, commonly called a Taguci cell, or its equivalent. Automatic correction is provided for variations in sensitivity of the semiconductor.

Talbot, U.S. Pat. No. 4,649,027 describes a battery-operated portable breath tester. The breath tester includes a housing which defines a sleeve for receiving a wand. The wand defines an internal sample chamber, with a lamp at one end for providing infrared energy and a detector at an opposite end for receiving the infrared energy after it has passed through the sample to be tested. The wand defines opening extending from the internal sample chamber to the outside of the wand. The wand has an external shape providing a snug fit within the sleeve. As the wand is moved within the sleeve, gas is purged from the wand. The wand is connected to the housing by means of an electrical coil. The housing encloses a digital voltmeter including a digital display for providing a test readout. The digital voltmeter includes an oscillator which is coupled through a frequency divider and a transistor switch to the lamp. The lamp is switched on and off in accordance with the frequency output of the frequency divider to modulate the infrared energy emitted from the lamp at a selected frequency. A voltage regulator is connected to the lamp, and the lamp and voltage regulator are located in heat-exchange relationship with the sample chamber. This aids in raising the temperature of the sample chamber during testing in order to alleviate condensation.

Lopez, U.S. Pat. No. 4,749,553 describes a breath alcohol detector for measuring and compensating for distance between the mouth of the individual exhaling breath into the ambient air and the detector, the atmospheric pressure, and the temperature. Blood alcohol content information is calculated using these compensation factors and a signal obtained from an electrochemical fuel cell which is indicative of the amount of alcohol or other gas contained in the sample. The detector also includes a reciprocally acting electromagnetically energized motor which drives a diaphragm pump to draw the sample into the electrochemical fuel cell.

Fukui, U.S. Pat. No. 4,849,180 describes an alcohol selective gas sensor including a detecting electrode and a semiconductor detecting element in contact with the detecting electrode, the semiconductor detecting element comprising tin oxide ($SnO_2$) and a metal oxide of at least one of alkaline earth metals (Be, Mg, Ca, Sr, Ba) carried by the tin oxide, the metal oxide being contained in an amount of about 0.5 mol % or above.

O'Donnell et al., U.S. Pat. No. 4,905,498 describes a gaseous detection system for detecting the existence of a certain gas and further the detection of a certain level or percentage of that certain gas within a certain environment. An example is use of the gas detection system in a motor vehicle to aid in determining when a driver of the motor vehicle may be driving under the influence of alcohol, and for providing an appropriate warning signal that may be viewed from the exterior of the motor vehicle. The system includes a sensor unit for sensing ethanol in the atmospheric contents of the motor vehicle's interior, for example, a unit for providing an actuation signal in response to the sensing unit, and a signal unit that generates a signal which can be utilized for many purposes, for example, causing at least some of the exterior lights on the motor vehicle to alternately flash on and off in a substantially non-standard pattern. The sensing unit may also be coupled with a digital read-out device or the like to indicate the amount of blood alcohol content of a person for evidentiary or like purposes.

Martin, U.S. Pat. No. 5,055,268 describes an air-borne chemical sensor system including a motor and impeller to draw an air sample into a housing containing a sensor which will provide a signal for display related to the amount of a particular air-borne chemical in a given air sample. The system is controllable by different duration activation of a single activating switch which can further control a secondary function, such as a flashlight.

Phillips, U.S. Pat. No. 5,220,919 describes a gaseous detection system for detecting the existence of a certain gas and further the detection of a certain level or percentage of that certain gas within a certain environment. An example is use of the gas detection system in a motor vehicle to aid in determining when a driver of the motor vehicle may be driving under the influence of alcohol, and for providing an appropriate warning signal that may be viewed from the exterior of the motor vehicle. The system includes a sensor unit for sensing ethanol in the atmospheric contents of the motor vehicle's interior, for example, a unit for providing an actuation signal in response to the sensing unit, and a signal unit that generates a signal which can be utilized for many purposes, for example, causing at least some of the exterior lights on the motor vehicle to alternately flash on and off in a substantially non-standard pattern. The sensing unit may also be coupled with a digital read-out device or the like to indicate the amount of blood alcohol content of a person for evidentiary or like purposes.

Forrester et al., U.S. Pat. No. 5,376,555 describes a method and infrared sensing device for determining the concentration of alveolar alcohol in a breath sample exhaled by a subject into an infrared sensing device. The presence of alcohol from the upper respiratory tract of the subject is detected by continuously monitoring alcohol and carbon dioxide, normalizing alcohol values with respect to carbon dioxide, calculating a difference between normalized alcohol concentration and carbon dioxide concentration over time, integrating (summing) the difference, and comparing the integrated difference with a threshold. This technique accurately and consistently detects the presence of mouth alcohol in the sample before the presence of carbon dioxide which originates in deep lung breath.

Steinberg, U.S. Pat. No. 5,743,349 describes a vehicle ignition interlock system including a non-invasive reader of a person's blood-alcohol concentration in combination with ignition interlock circuitry that prevents operation of a vehicle by an intoxicated person. The non-invasive blood-alcohol concentration reader, termed alcoh-meter, utilizes optical spectroscopic electromagnetic radiation technology to determine the alcohol levels in the blood. The alcoh-meter is preferably a dash mounted sensor for receiving a person's finger and absorbing incident light from a multiple wavelength light source and causing a light absorption reading to be generated based on the person's blood alcohol concentration in the finger tissue. After registering a reading, the results are compared electronically against a table of impaired/non-impaired levels of blood alcohol concentration. The impaired/non-impaired results are communicated to interlock circuitry that either enables, or disables start-up of the vehicle. If an impaired status is determined, the results are displayed instructing the operator to wait, or find a non-impaired operator.

Sohèege et al., U.S. Pat. No. 6,075,444 describes an arrangement for blocking the operation by an intoxicated operator of a machine or a motor vehicle. The arrangement has a measuring apparatus which determines the blood alcohol content of the operator and an evaluation unit connected to the machine or motor vehicle. The evaluation unit receives measurement data supplied by the measurement apparatus and enables the machine or motor vehicle when the measurement data satisfies at least one predetermined condition. The arrangement is improved in that the sobriety of the operator is recognized before the starting operation of the machine or motor vehicle without it being necessary to supply a breath sample. The measuring apparatus includes a gas sensor which is a sensor for measuring the blood alcohol content via permeation through the skin of the operator. The measuring apparatus is configured so that it can be worn by the operator preferably on the leg or arm.

Kaplan, U.S. Pat. No. 6,097,480 describes a vehicle interlock system which utilizes non-invasive, optically based methods for detecting and measuring levels of certain target chemical substances in the blood or tissues of a user in preventing operation of the vehicle by persons exhibiting higher (or lower) than prescribed levels of such chemicals. The system of the present invention is not limited to simply measuring blood alcohol levels as are presently available breathalizer-based interlock systems, but lends itself to use in detecting unacceptable systemic levels of virtually any chemical for which the system if programmed to measure. In addition, the present system includes components for positively identifying, and during the course of vehicle operation, re-identifying the intended user and alcohol or drug user testee.

Kuennecke, U.S. Pat No. 6,183,418 describes the process for detection and for quantitative determination of substances emitted or perspired through the skin is derived from flow diffusion analysis. The measuring system conceived for this purpose uses a diffusion half cell through which an acceptor medium flows and which is closed by a membrane. For the duration of the measurement, the membrane is brought into contact with the skin or a closed gas volume formed over the skin. With the process and the related measuring system, the blood alcohol level can be determined with a good degree of precision indirectly via the quantity of (gaseous) ethanol emitted through the skin.

Duval, U.S. Pat. No. 6,620,108 describes an apparatus and method for assuring that a machine operator is not under the influence of a chemical, comprising a first sensor positioned proximally to the machine operator and adapted for measuring a vapor concentration proximal thereto, a second sensor positioned distally from the machine operator and adapted for measuring the vapor concentration distally from the operator, a device for comparing the proximal and distal vapor concentrations, and an automated remediating element responsive to the comparing device when the ratio of the first and the second vapor concentrations are within a specified range.

Our prior art search with abstracts described above primarily teaches the use of analyzing vapors produced in the exhalant of an individual. Thus, the prior art shows several solutions to the collection and analysis of minute partial pressures of vapors. However, the prior art fails to teach a simple system that can avoid the use of deliberate breath analysis and yet be inexpensive by avoiding the very high sensitivity required of room air analyzers. The present solution employs a steering wheel having an integral infrared spectrometer which is able to detect alcohol in perspiration on a users hands, i.e., excreted through the skin; analyze the vapors and produce a control signal. This enablement allows automatic monitoring and the initiation of remedial actions when necessary for the safety of the individual and the public at large. The present invention fulfills these needs and provides further related advantages as described in the following summary.

SUMMARY OF THE INVENTION

Data has been collected on the number of accidents and accident related deaths on U.S. highways each year that are, at least in part, related to alcohol or other substances within the blood stream of drivers. This data shows that it would be wise to take steps to prevent motorists from driving when they are under the influence of such substances. One solution to this problem is to install a device in existing and new automobiles, and other types of vehicles that will monitor and possibly prevent such driving. The present invention teaches certain benefits in construction and use of such devices which give rise to the objectives described below and forms at least a partial solution to this problem.

The invention is a detection system installed into a steering wheel of a vehicle wherein an infrared spectrometer is used to detect ethanol vapors emitted by the driver's hands. Such vapors may also be from the driver's breath, clothing, and other exposed skin areas that come into contact or merely just close proximity to the light source of the spectrometer. It may be used on automobiles, trucks, buses, boats and other vehicles. Such detection may be used to trigger a warning or other action, including shutting down the ignition system of the vehicle. In a best mode preferred embodiment of the present invention, a solid state infrared spectrometer is made an integral part of a steering wheel assembly. The spectrometer is preferably a part of a detection and alarm system built into the vehicle and the spectrometer detector is preferably in communication with other circuitry components of the detection and alarm system by wireless means. Such circuitry may be placed behind a control or dash board of the vehicle, and may be enabled for controlling an ignition circuit of the vehicle. Alternately, the control circuit might control audible or visual devices to inform the driver that he/she is driving dangerously, or might control other devices as deemed necessary to protect the driver, any passengers and the general public.

A primary objective of the present invention is to provide an apparatus and method of use of such apparatus that yields advantages not taught by the prior art.

Another objective is to assure that an embodiment of the invention is capable of integrating vapor detection with a steering wheel assembly.

A further objective is to assure that the vapor of choice is detected by the steering wheel assembly.

A still further objective is to assure that an electrical signal is generated by the spectrometer vapor detector so as to generate an alert signal.

Other features and advantages of the embodiments of the present invention will become apparent from the following more detailed description, taken in conjunction with the accompanying drawings, which illustrate, by way of example, the principles of several possible embodiments of the invention.

BRIEF DESCRIPTION OF THE DRAWINGS

The accompanying drawings illustrate the best mode embodiments of the present invention.

In such drawings.

DETAILED DESCRIPTION OF THE INVENTION

The above described drawing figures illustrate the present invention in two of its preferred, best mode embodiments, which is further defined in detail in the following description. Those having ordinary skill in the art may be able to make alterations and modifications in the present invention without departing from its spirit and scope. Therefore, it must be understood that the illustrated embodiments have been set forth only for the purposes of example and that they should not be taken as limiting the invention as defined in the following.

Here, and in the following claims, "light" refers to all electromagnetic waves that can be produced, detected, or controlled by optical means, and includes infrared (IR), visible light, or ultraviolet (UV) unless otherwise specified; "pyramid detector" means any detector with one or more light-to-electricity converting transducers deployed adjacent to a hole; and "window" means an opening or interruption in an opaque wall that allows a light beam to pass through.

Figure 1:
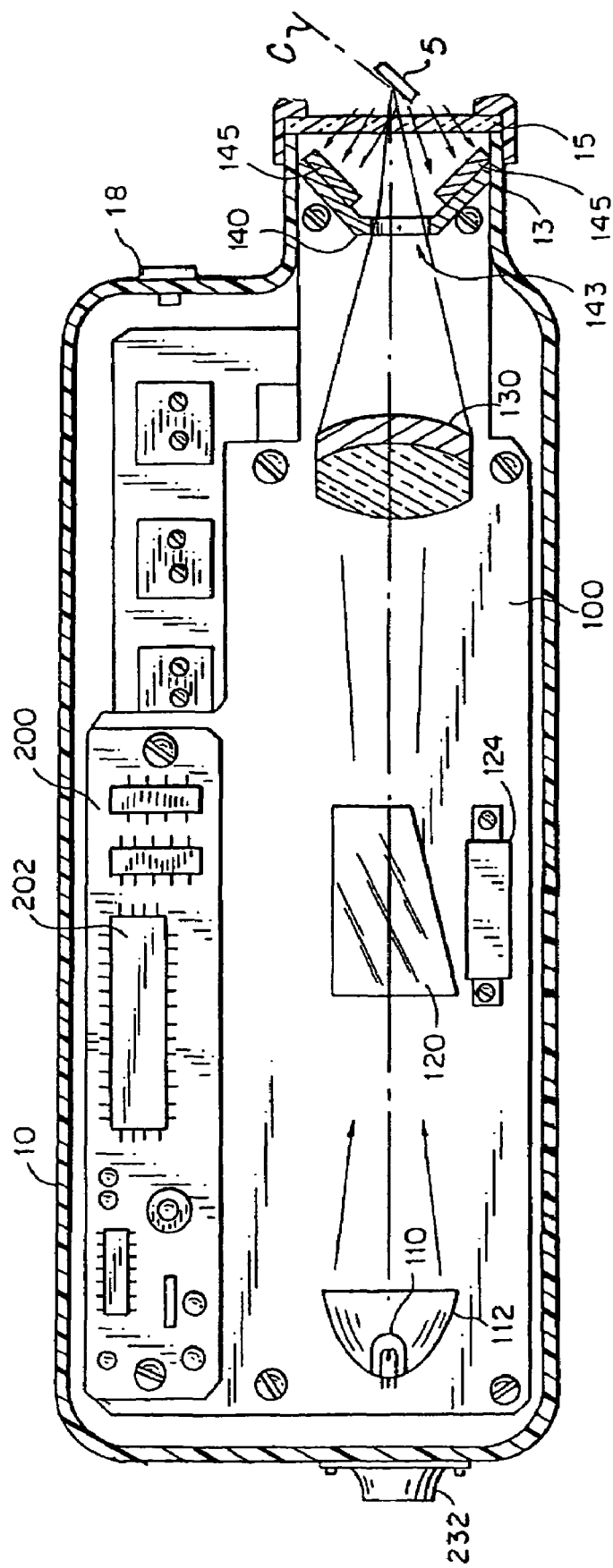
FIG. 1 is a sectional elevational view of an infrared spectrometer of the invention.
Figure 2:
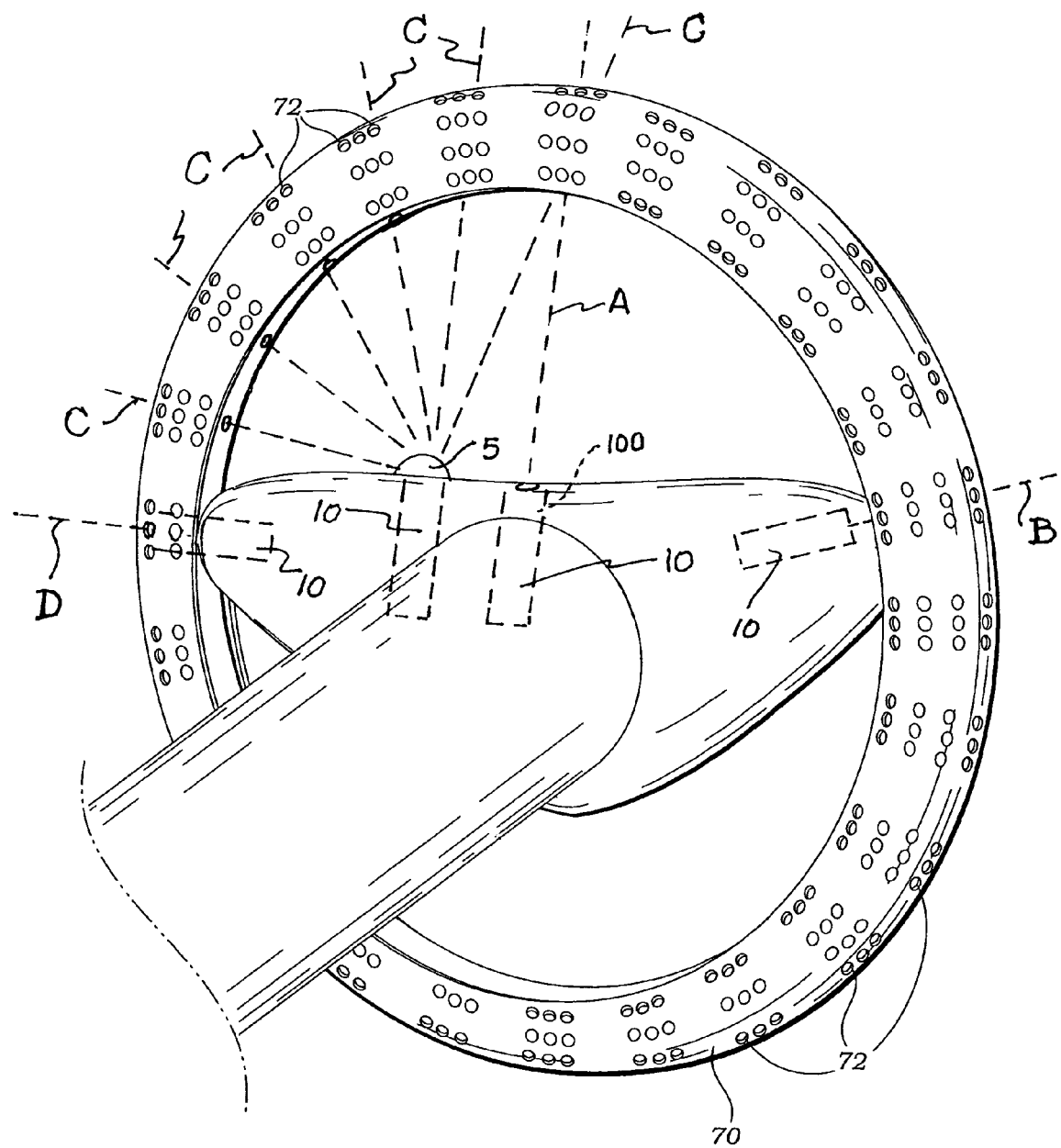
FIG. 2 is a perspective view of a steering wheel and steering column structures showing three possible locations for mounting the spectrometer for aligning its output signal with holes in the steering wheel.

FIG. 1 shows the interior of an AOTF spectrometer according to the Levin et al reference, and which is used to identify an unknown material. The spectrometer is housed in a housing 10 which includes a window 15. The window 15 is preferably one which is opaque or at least partially opaque to visible light, but transparent to IR. The housing 10 may be made quite small and can easily fit within the central portion of most automobile steering wheel assemblies, as shown in FIG. 2. The typical steering wheel mounted horn actuator voltage is used to power the spectrometer's circuits for making measurements.

Inside the housing 10 are an optical bench 100 and a single printed circuit board 200 which contains all of the system electronics. A computer 202 for data analysis is built into the device as shown. A remote computer is accessed through the port 232 via conductor wires, or port 232 may be a radio transmitter for wireless communication to a control circuit 60 shown in FIG. 3.

The optical module consists of several optical components mounted on the bench 100, which is preferably a solid plate, e.g., formed of aluminum. The optical components include the following elements, provided in a linear relationship: a light source or lamp 110 (a tungsten-halogen lamp, for example); an AOTF crystal and case 120; a focusing lens 130; and a reflectance detector 140. The AOTF crystal, preferably including $TeO_2$ (tellurium dioxide), is about one inch long and one-half inch wide. The AOTF 120 includes a piezo-electric transducer, preferably of LiNo, bonded to one face of the bi-refringent $TeO_2$ crystal. A small RF power amplifier 124 is mounted in close proximity to the crystal 122; it produces about 1 Watt of RF power in the frequency range from 20 to 100 MHz.

The lamp 110 is contained within a parabolic mirror 112 in order to collimate the beam. This beam then passes through the AOTF crystal 120, and emerges as a tuned, narrow-band infrared beam approximately 8 by 8 mm in size. This beam passes through the lens 130, which focuses the beam through the window 15, onto the sample to be analyzed.

At the end of the optical bench is mounted a reflectance detector 140. This detector may include up to four or even more lead sulfide (PbS) or lead selenide (PbSe) flat detector elements or transducers 145, each about 10 by 10 mm in size and facing the sample through the window 15. The detectors are arranged on the inner surface of a 45 degree pyramid or cone. The cone has a hole 143 at the apex for the light beam to pass through. The base of the pyramid faces the sample. Therefore, the infrared beam strikes the sample, and the diffusely reflected light from the sample (indicated by arrows in FIG. 1) is detected by the detector elements 145.

As indicated above, the housing includes the window 15, which in the preferred embodiment is a transparent element having broad-band IR transmission but little visible transmission; it appears black. The optical properties of the window 15, like those of the other optical elements, are compensated for automatically when the device is calibrated using a pure white ceramic material.

The small printed circuit board 200 mounted above the optical bench 100 contains all of the system electronics 204, including: a digitally-controlled frequency synthesizer (used to generate the RF frequencies to tune the AOTF), a detector preamplifier and bias voltage, an A/D converter, and computer interface (e.g., RS-232). In addition, there is an amplitude modulator (and de-modulator) circuit which modulates the RF signal at about 5 kHz for improved signal to noise ratio. The frequency synthesizer is preferably a lower-frequency generator (e.g., up to 50 MHz) driving a doubler; this arrangement uses less power.

Figure 3:
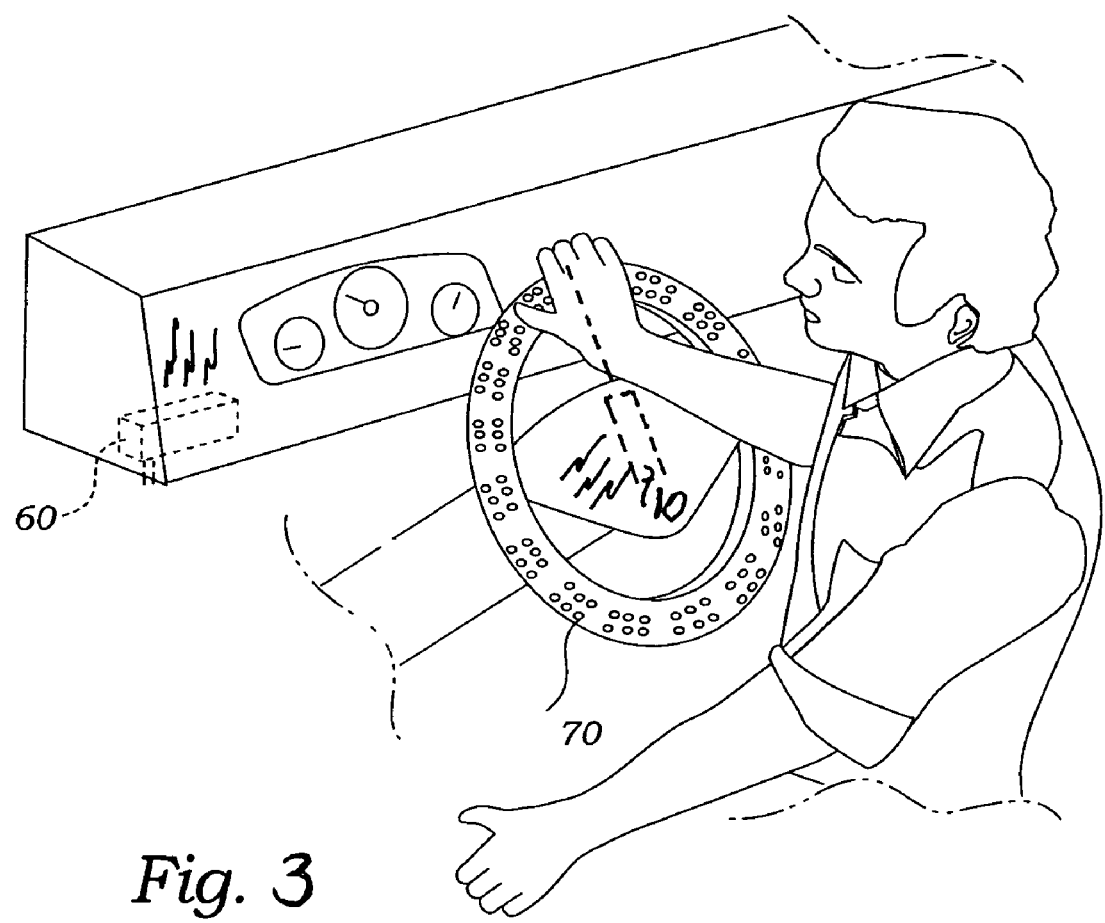
FIG. 3 is a perspective view of the invention as used in a vehicle.

As shown in FIG. 2, the spectrometer described above is mounted within the steering wheel assembly 70. In one embodiment, the spectrometer housing 10 is mounted for emitting along light path "A" which is aligned with holes 72 in the steering wheel so that the light is able to strike the hand of a driver. In another embodiment, the spectrometer housing 10 is mounted for emitting along light path "B," again, wherein the path transits holes 72. In a still further alternative embodiment, the housing 10 is placed for emitting light as reflected from mirror 5 (FIG. 1). Mirror 5 is motor driven to move rapidly over a range of angles thereby reflecting the spectrometer's output light beam to positions shown by "C" in FIG. 2. Finally, in a final embodiment, the housing 10 is positioned so that the output window 15 is in actual contact or near contact with a hand of the driver, i.e., light path "D." Holes 72 are placed in the steering wheel 70 and are through holes whereby the output light beam "A," "B," "C," or "D" is able to pass through the steering wheel 70 and strike the hand of a driver, as shown in FIG. 3. The light that is scattered back toward the spectrometer passes, again, through the holes 72 and is conducted directly, or by mirror 5 to sensors 145. With respect to the embodiment producing the moving light beam "C," it may be seen that no matter where the driver places his/her hands, the light beam "C" will strike at least one of them causing a spectrometer reading. The reading is then transmitted, preferably by radio waves, as shown in FIG. 3, to the alarm circuit 60 which may be placed anywhere within the vehicle. Since the object of this invention is to detect only those spectral lines associated with ethanol, the spectrometer may be miniaturized by dedicating it to only that one task.

The preferred method of the present invention for identifying a material composition of a sample comprises, providing the spectrometer of this invention within the steering wheel assembly with placement as shown in FIG. 2. Disposing a window of the spectrometer in an exterior position on the steering well assembly, in optical alignment with a hand of a driver of the vehicle or in contact or near contact with a surface of the hand. Projecting a spectral light beam onto the sample and receiving reflected light from the sample at detectors in the spectrometer. The method further includes spectrally analyzing the reflected light for a selected substance such as ethanol alcohol, and upon detection of the substance at a selected magnitude, sending an alarm signal to an alarm circuit.

The enablements described in detail above are considered novel over the prior art of record and are considered critical to the operation of at least one aspect of one best mode embodiment of the instant invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or elements of the embodiments of the herein described invention and its related embodiments not described are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the invention and its various embodiments or that a single element may be substituted for two or more elements in a claim.

Changes from the claimed subject matter as viewed by a person with ordinary skill in the art, now known or later devised, are expressly contemplated as being equivalents within the scope of the invention and its various embodiments. Therefore, obvious substitutions now or later known to one with ordinary skill in the art are defined to be within the scope of the defined elements. The invention and its various embodiments are thus to be understood to include what is specifically illustrated and described above, what is conceptually equivalent, what can be obviously substituted, and also what essentially incorporates the essential idea of the invention.

While the invention has been described with reference to at least one preferred embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A substance detection apparatus system in a vehicle for light reflectance measurements, the apparatus system comprising: an infrared spectrometer mounted in a steering wheel assembly wherein an output light beam of the spectrometer is directed through holes in the steering wheel assembly for producing reflected light according to the spectral lines associated with a substance in contact with the steering wheel assembly and for producing an alarm signal when the spectral lines of the reflected light match one of a stored alarm spectrum; and further comprising a mirror controlled by a motive means for sweeping the output light beam over an arc to direct the light beam through a plurality of the through holes in the steering wheel assembly.

2. The apparatus system of claim 1 further comprising an alarm circuit in communication with the spectrometer.

3. The apparatus system of claim 2 further comprising a radio wave transmitter in signal communication with the spectrometer and a radio wave receiver in signal communication with the alarm circuit.

4. The apparatus system of claim 1 wherein the spectrometer is positioned for near contact with an outer surface of the steering wheel.

5. A method of identifying a material composition of a sample, comprising:
   (a) providing a spectrometer in a steering wheel assembly, including a window disposed in an exterior position in one of: i) optical alignment and ii) against a surface of the sample;
   (b) projecting a spectral light beam onto the sample;
   (c) receiving reflected light from the sample;
   (d) spectrally analyzing the reflected light for a selected substance; and
   (e) upon detection of the substance at a selected magnitude, sending an alarm signal to an alarm circuit.

* * * * *